(12) United States Patent
Bader

(10) Patent No.: US 10,022,324 B2
(45) Date of Patent: Jul. 17, 2018

(54) POLYSIALIC ACID-POLYCAPROLACTONE MICELLES FOR DRUG DELIVERY

(71) Applicant: Rebecca Bader, Billerica, MA (US)

(72) Inventor: Rebecca Bader, Billerica, MA (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 15/029,652

(22) PCT Filed: Oct. 15, 2014

(86) PCT No.: PCT/US2014/060580
§ 371 (c)(1),
(2) Date: Apr. 15, 2016

(87) PCT Pub. No.: WO2015/057764
PCT Pub. Date: Apr. 23, 2015

(65) Prior Publication Data
US 2016/0243037 A1    Aug. 25, 2016

Related U.S. Application Data

(60) Provisional application No. 61/891,052, filed on Oct. 15, 2013.

(51) Int. Cl.
| | | |
|---|---|---|
| *A61K 9/107* | (2006.01) | |
| *A61K 31/366* | (2006.01) | |
| *A61K 31/573* | (2006.01) | |
| *A61K 31/728* | (2006.01) | |
| *A61K 38/13* | (2006.01) | |
| *A61K 47/34* | (2017.01) | |
| *A61K 47/36* | (2006.01) | |
| *A61K 31/726* | (2006.01) | |
| *A61K 9/00* | (2006.01) | |
| *A61K 9/19* | (2006.01) | |

(52) U.S. Cl.
CPC .......... *A61K 9/1075* (2013.01); *A61K 9/0019* (2013.01); *A61K 9/19* (2013.01); *A61K 31/366* (2013.01); *A61K 31/573* (2013.01); *A61K 31/726* (2013.01); *A61K 31/728* (2013.01); *A61K 38/13* (2013.01); *A61K 47/34* (2013.01); *A61K 47/36* (2013.01)

(58) Field of Classification Search
USPC ..................................................... 424/78.17
See application file for complete search history.

(56) References Cited

U.S. PATENT DOCUMENTS

| | | | | |
|---|---|---|---|---|
| 5,522,842 A | * | 6/1996 | Shalaby ................. | A61L 17/12 525/354 |
| 8,936,635 B2 | | 1/2015 | Kaesemeyer | |
| 9,241,913 B2 | | 1/2016 | Bader | |
| 2004/0247624 A1 | * | 12/2004 | Unger ..................... | A61K 9/19 424/400 |
| 2006/0177416 A1 | * | 8/2006 | Turnell ................ | A61K 9/1075 424/78.27 |

OTHER PUBLICATIONS

Oh et al., Journal of Biomaterials Research, "Control of the molecular degradation of hyaluronic acid hydrogels for tissue augmentation", 2007, 685-693.*
Wilson et al. Synthesis and evaluation of cyclosporine A-loaded polysialic acid-polycaprolactone micelles for rheumatoid arthritis. European Journal of Pharmaceutical Sciences 51:146-156. Sep. 27, 2013 (online). retrieved on [Dec. 12, 2014] Retrieved from the Internet, URL: http://www.sciencedirect.com/science/article/pii/S0928098713003679>. entire document.
PureVolume. General: Tofacitinib Fluorescently labeled PSA PCL was prepared by dissolving mg of. Blog Post. Dec. 22, 2013 [retrieved on Dec. 12, 2014] Retrieved from the Internet URL: http:www.purevolume.com/listeners/fyPetrufyFreeabda/posts/596102/Tofacitinib+Fluorescently+labeled+PSA+PCL+was+prepared+by+dissolving+mg+of. entire document.
International Search Report Form PCT/ISA/220, International Application No. PCT/US2014/060580, pp. 1-6, dated Jan. 23, 2015.

* cited by examiner

*Primary Examiner* — Lezah Roberts
(74) *Attorney, Agent, or Firm* — Bond Schoeneck & King, PLLC; George McGuire

(57) ABSTRACT

PSA-PCL micelles were developed as carrier systems for pharmaceutical drugs. As an example, cyclosporine A (CyA) was encapsulated in the micelles and physical characterization, including size and zeta potential, demonstrated that the micelles possess favorable properties for drug delivery. In vitro studies verified that rheumatoid arthritis synovial fibroblasts are able to internalize the CyA-loaded micelles. CyA was released from the PSA-PCL micelle upon uptake and subsequently, partitioned into the phospholipid membrane. The PSA-PCL micelles also demonstrated improved therapeutic efficacy in drug delivery when used to deliver statins and disease modifying anti-rheumatic drugs (DMARDs).

14 Claims, 14 Drawing Sheets

POLYSIALIC ACID-POLYCAPROLACTONE MICELLES FOR DRUG DELIVERY

CROSS-REFERENCE TO RELATED APPLICATIONS

This invention claims priority to U.S. Provisional Application No. 61/891,052, filed on Oct. 15, 2013.

STATEMENT REGARDING FEDERALLY SPONSORED RESEARCH OR SUPPORT

This invention was made with government support under Grant No. EFRI-1137186 awarded by the National Science Foundation (NSF). The government has certain rights in the invention.

BACKGROUND OF THE INVENTION

1. Field of the Invention

The present invention relates to drug delivery systems and, more specifically, to polysialic acid and polycaprolactone micelles for the delivery of hydrophobic drugs.

2. Description of the Related Art

Due to the high cost and lengthy implementation timeline involved with drug discovery, drug delivery may serve as an alternative method to advance pharmaceutical sciences and human health. In addition, a numbers of therapeutics are characterized by poor bioavailability, unfavorable biodistribution, and high cytotoxicity, particularly when administered systemically. Drug carrier systems are needed to improve drug efficacy and reduce cytotoxicity in the human body. To date, many studies have been conducted based on the theory proposed by Paul Ehrlich to develop therapeutics which can be site-specifically delivered to the target tissue, with reduced accumulation in the healthy tissue. Most of these delivery systems are designed with the advantages of increased drug solubility, prolonged circulatory stability, and high tissue specificity.

Among various nanoparticle systems, polymeric micelles have drawn much attention for the encapsulation of hydrophobic. These micelles are formed from macromolecules composed of hydrophobic and hydrophilic segments. In an aqueous environment, the amphiphilic polymers self-assemble into a core-shell structure due to the aggregation of the hydrophobic moieties. Thus, hydrophobic drugs can be physically encapsulated into the core via hydrophobic interactions. In general, micelles provide therapeutics with improved solubility, enhanced stability, and an extended circulation time.

When administered systemically, drug delivery systems without sufficient hydrophilicity to reduce the recognition and binding of plasma proteins are often eliminated rapidly by the reticuloendothelial system (RES). Thus, by increasing the surface hydrophilicity, the rate of elimination can be decreased and the circulation time can be prolonged, thereby improving the likelihood that the drugs will reach the target disease tissues. To date, poly(ethylene glycol) (PEG)-based modification has been the most common method to improve hydrophilicity and provide the drugs with so-called "stealth" properties to evade detection by the RES. However, PEG may not be the ideal solution due to a non-biodegradable backbone, evidence of continuous accumulation inside the body, and problems with immunogenicity. Moreover, the PEG coating is known to interfere with some of the steps involved in drug delivery. After localization to the diseased tissue, PEG coatings have been reported to hinder drug release from the carrier systems and reduce requisite drug-cell interactions.

As an alternative, polysialic acid (PSA) is a relatively unexplored natural, non-toxic, and biodegradable polysaccharide that has the potential to prolong the circulation time of associated drugs and provide additional benefits. PSA is a linear homopolymer of $\alpha$-2, 8-linked 5-Nglycolyneuraminic acid (Neu5Ac) and is widely produced by pathogenic bacteria, as well as the cells of vertebrates and higher invertebrates. Thus, PSA is highly involved and has multifarious roles in a wide variety of biological, immunological, and pathological processes. Some pathogenic bacteria can escape the host immune system and evade the host tissues by producing a thick PSA coating on the cell wall. In mammals, the major function of PSA is believed to be the anti-adhesive properties that can change the cell-cell and cellextracellular matrix interaction and promote neural plasticity. PSA acts as a post-translational modification of neural cell adhesion molecules (NCAM), and the fifth Ig domain of NCAM is able to carry PSA at a high loading capacity. The significant negative charge and large hydrated volume of PSA can reduce NCAM-mediated adhesion and enable neuron cell migration. Typically, PSA expression is down-regulated in most tissues of the adults. However, during the neural injuries and tumorigenesis, PSA is expressed on the cell surfaces, which serves to alter cellular interactions to abrogate cell adhesion and facilitate cell migration. The anti-adhesive properties are further supported by immune studies that demonstrate that the removal of PSA generates an "eat me" signal to macrophages to recognize and clear the uncoated bacteria, excess proteins, or dead cells.

Due to the natural anti-adhesive properties highlighted above, PSA has drawn attention in the field of drug delivery. Based on a series of studies on sialylated or polysialylated proteins, it has been proposed that PSA was a potential material to increase the stability and circulation time of therapeutics inside the bodies. PSA-drug conjugation has been used to increase the half-life of insulin, asparaginase, and catalase. As a result, immunogenicity and antigenicity were reduced, and the efficacy of the proteins was improved. To date, several PSA-protein conjugates and Neu5Ac derivatives have been developed as vaccines and therapeutic agents.

Compared to other drug delivery systems, nanoparticle-based targeted drug delivery systems have been shown to accumulate passively within tumor tissue and inflamed tissue due to the enhanced permeability of the leaky vasculature. Micelles from PSA modified with a long chain hydrocarbon, decylamine have been developed. Despite possessing the necessary physical properties in regards to size and surface charge, these micelles were cytotoxic towards a synovial fibroblast cell line.

BRIEF SUMMARY OF THE INVENTION

The present invention comprises a delivery system for a therapeutic compound using a micelle having a backbone of polymerized sialic acid monomers. Amine terminated polycaprolactone grafted to a portion of the sialic acid monomers. The sialic acid monomers and polycaprolactone are present in a weight ratio of 4 to 1 and the portion of sialic acid monomers that are grafted with the amine terminated polycaprolactone is about one percent. The resulting micelles have a diameter of 73.8+/−14.2 nanometers at a concentration of 1 milligram per milliliter and a temperature of 25° C. A therapeutic compound may then be loaded into the micelles to a capacity of 0.1 milligrams per milligram of micelle, resulting in micelles having a diameter of 107+/− nanometers at a concentration of 1 milligram per milliliter and a temperature of 25° C. The micelles may further comprise a receptor agonist tethered to a portion of the polysialic monomers. For example, the receptor agonist may be a hyaluronic acid oligomer tethered to a plurality of the polysialic monomers by an adipic dihydrazide, such as less than one percent of the polysialic monomers. An antirheumatic drug, such as dexamethasone, may be loaded into the micelles having the hyaluronic acid oligomer to a capacity of 0.1 milligrams per milligram of micelle to produce micelles loaded with dexamethasone and having a diameter of about 150 nanometers. Loaded micelles may then be used to more effectively deliver the loaded therapeutic compound by administering the loaded micelles to a patient.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
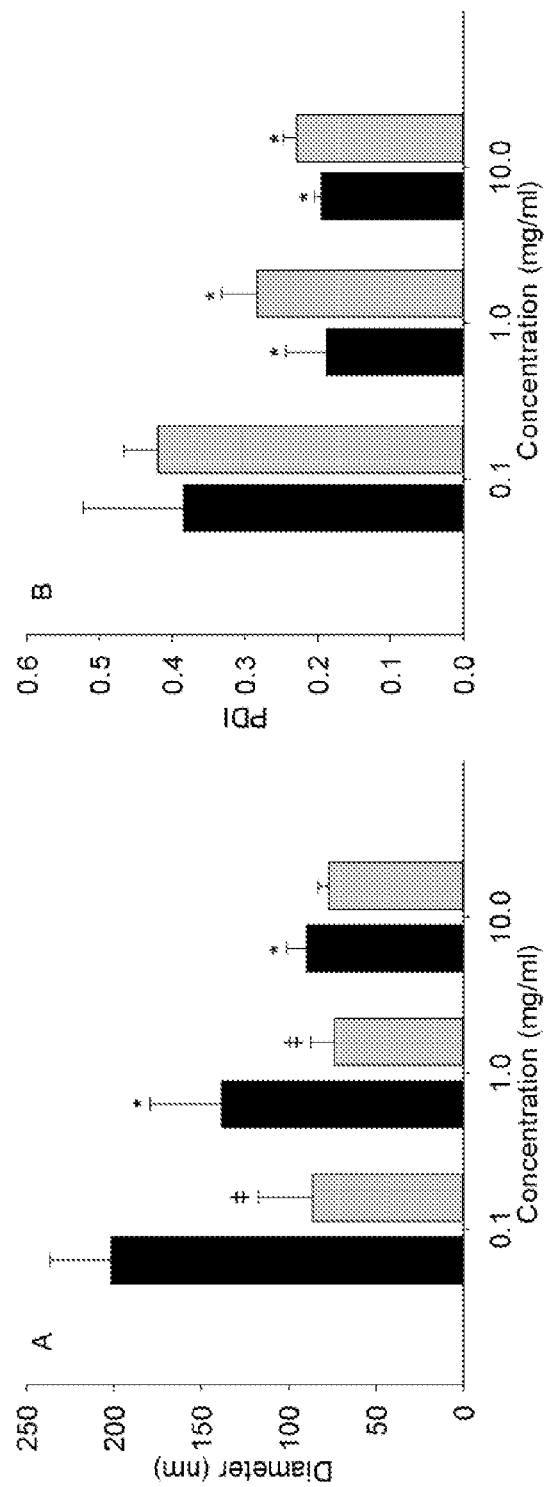

FIG. 3 is a graph of dynamic light scattering that was used to determine the size (A) and distribution (B) of PSA-PCL micelles at concentrations above the CMC at 25° C. (gray) and at 37° C. (black). * indicates a significant difference ($p<0.05$) relative to PSA-PCL micelles at a concentration of 0.1 mg/mL at the same temperature, as determined using one-way ANOVA, followed by post hoc Fisher's LSD. ‡ indicates a significant difference relative to PSA-PCL micelles at the same concentration at a temperature of 37° C., as determined by Student's t test.

Figure 4:
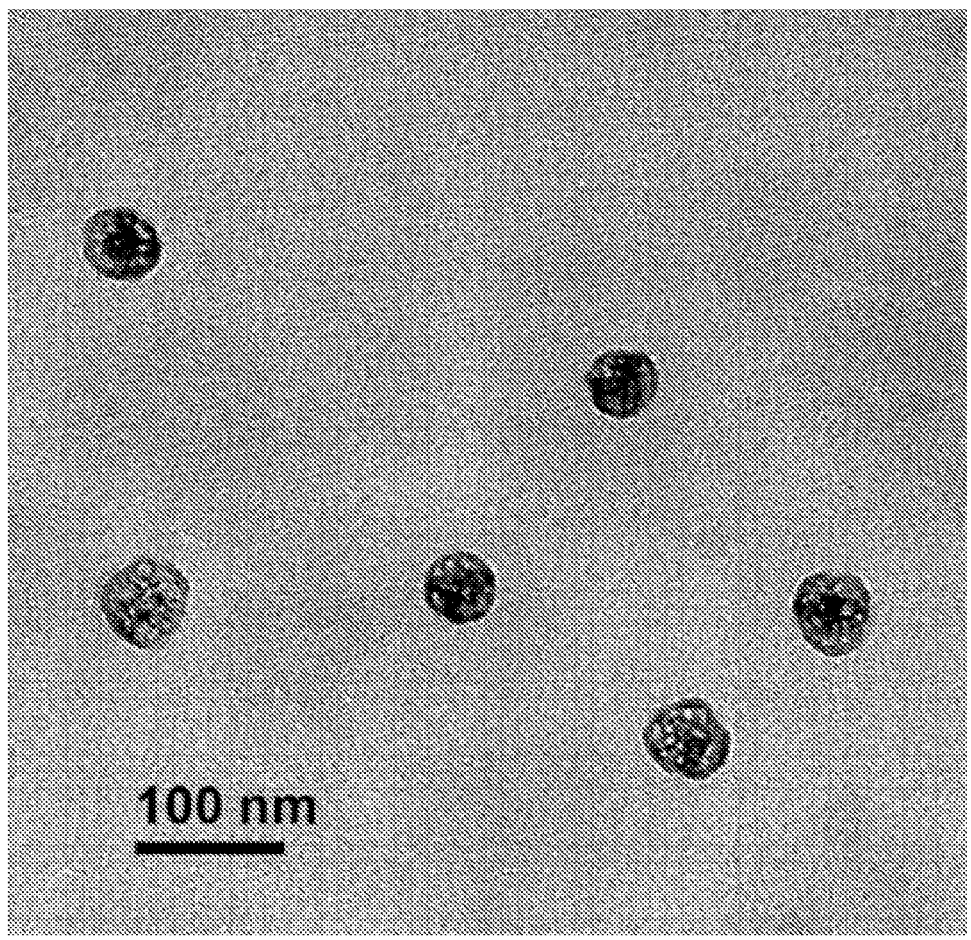

FIG. 4 is a micrograph of transmission electron microscopy used to confirm that spherical micelles with a size of approximately 70 nm were obtained via self-assembly of PSA-PCL.

Figure 5:
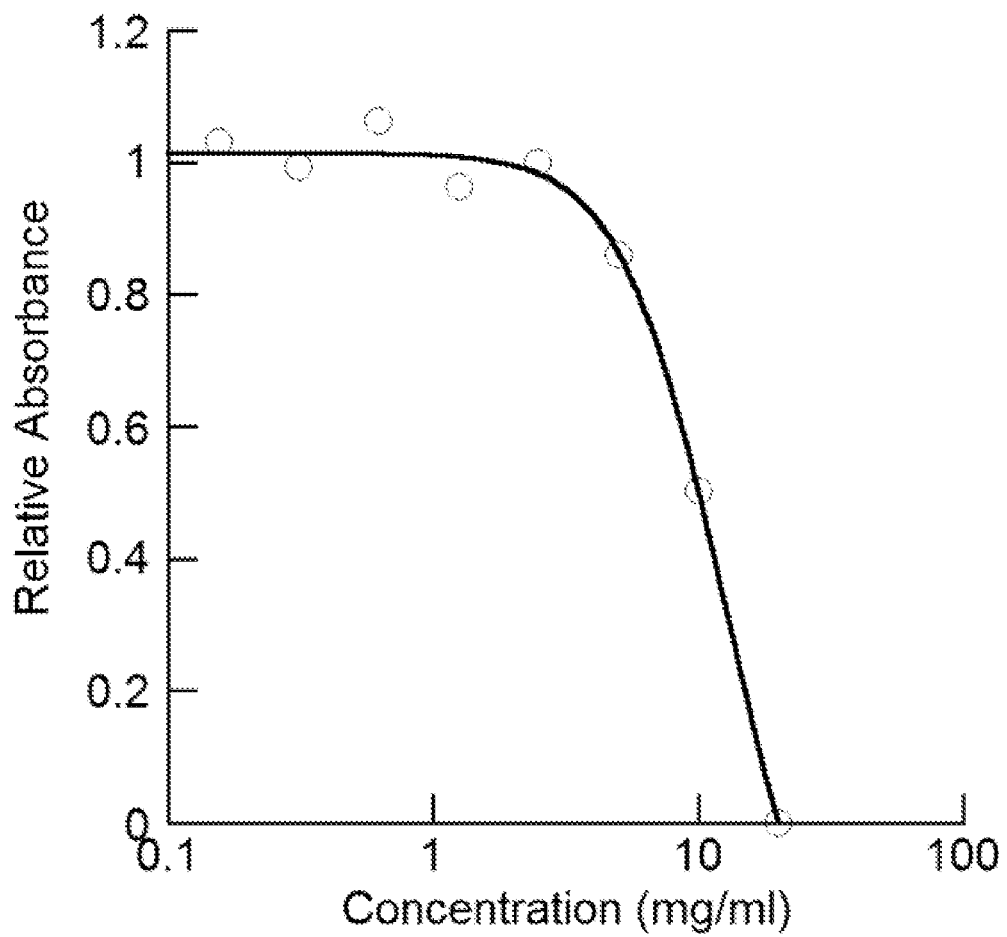

FIG. 5 is a representative plot illustrating the use of the WST-8 assay to assess PSA-PCL cytotoxicity towards the SW982 synovial cell line. A four parameter logistic curve fit was used to determine an $IC_{50}$ of 10.5±1.7 mg/ml.

Figure 6:
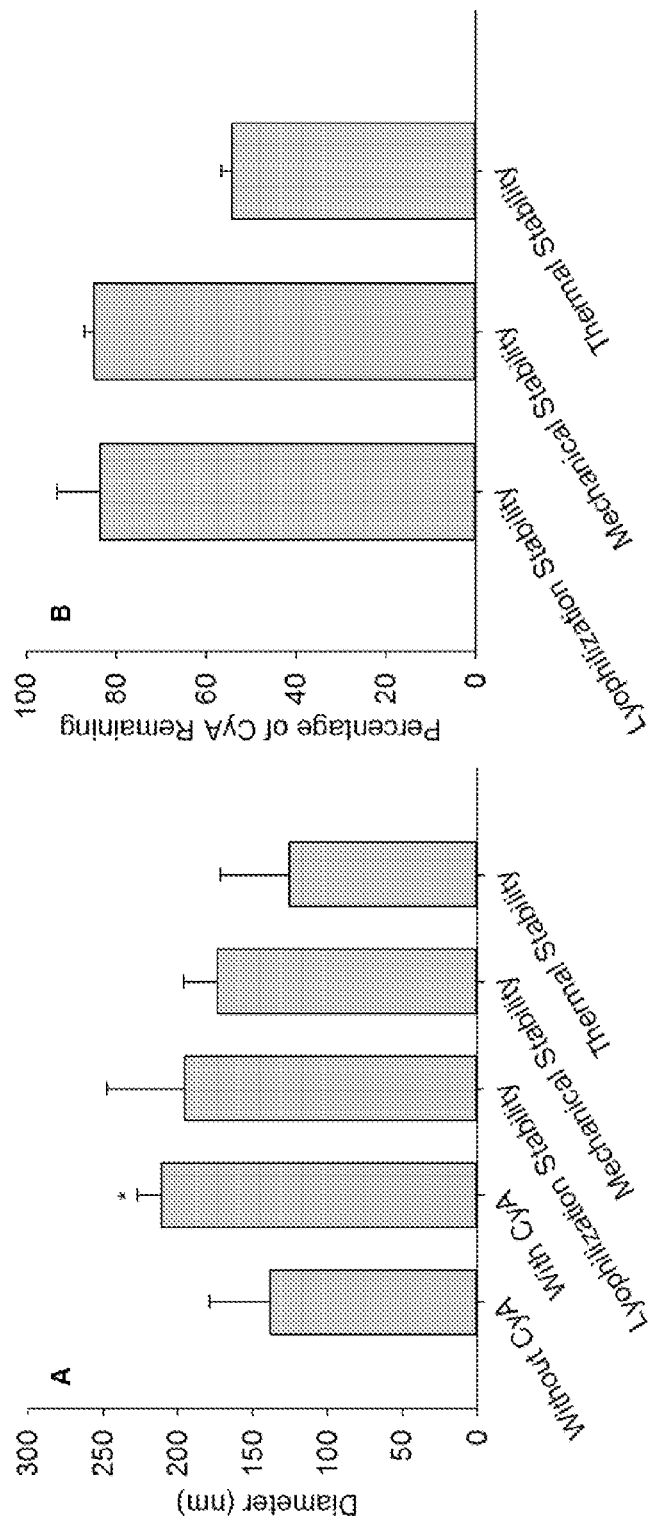

FIG. 6 is a chart showing mechanical and thermal stability assessed via changes in (A) the size of CyA-loaded PSA-PCL micelles and (B) the percentage of encapsulated of CyA. * indicates a significant difference relative to PSA-PCL micelles without encapsulated CyA, as determined by Student's t test.

Figure 7:
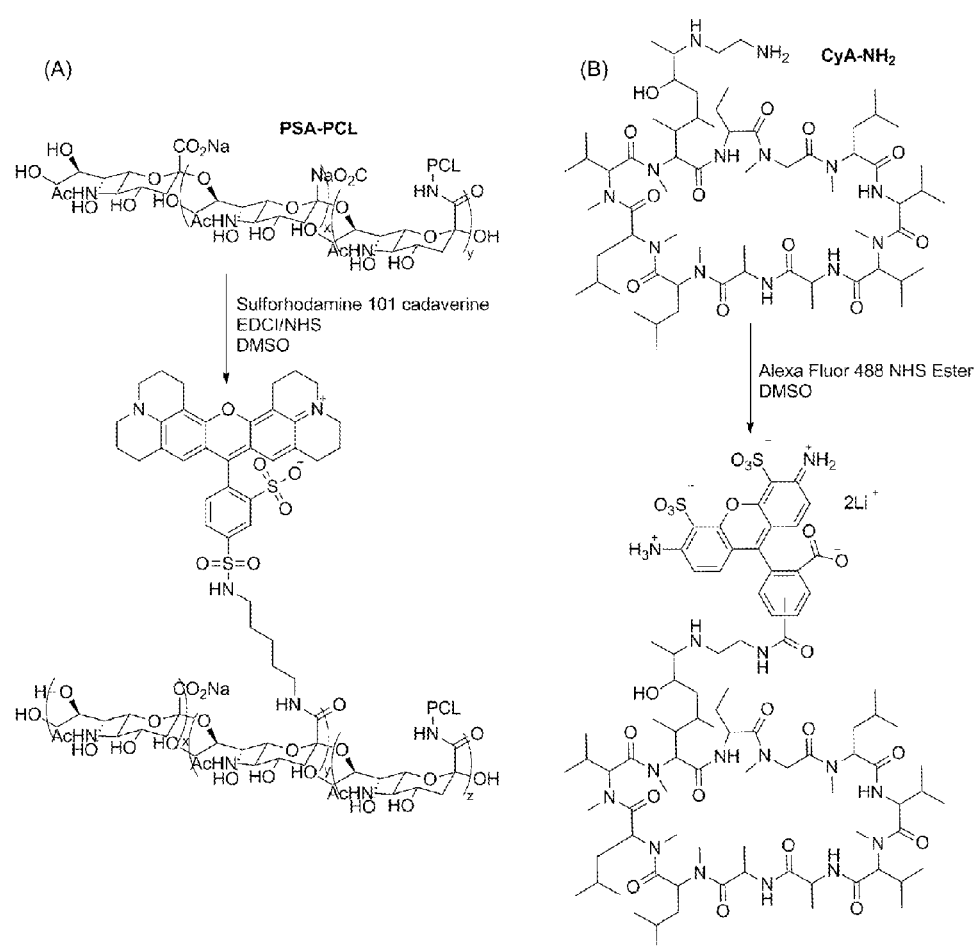

FIG. 7 is a series of schematics showing the synthesis of fluorescently tagged PSA-PCL and CyA. (A) PSA-PCL was conjugated to sulforhodamine 101 cadaverine, while (B) CyA modified to include a free amine moiety was linked to Alexa Fluor® 488.

Figure 8:
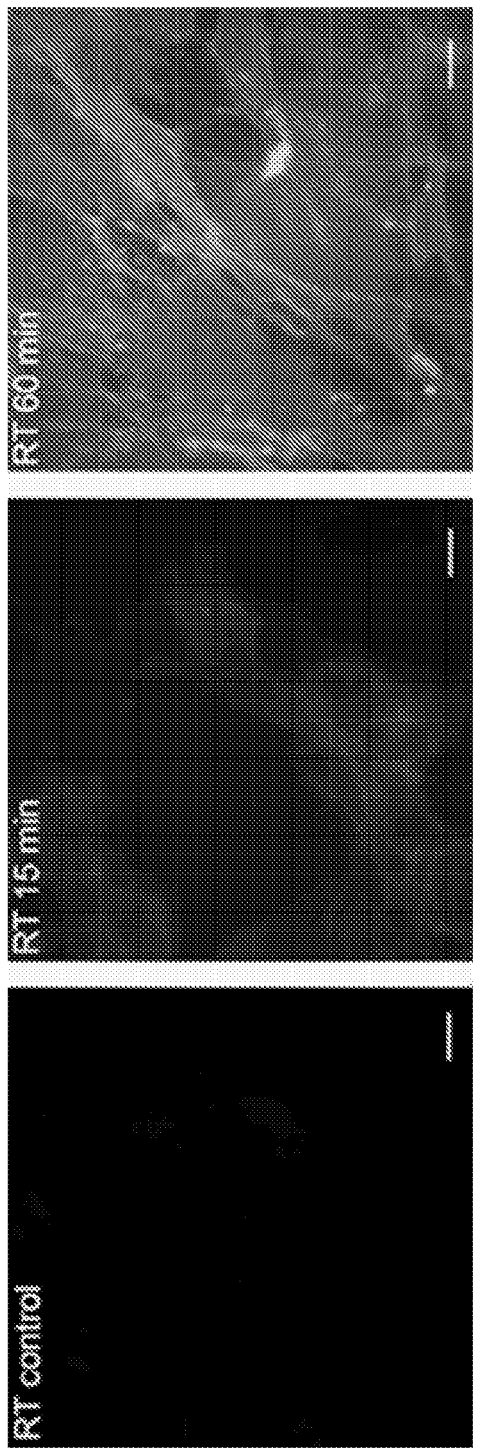

FIG. 8 is a series of micrographs showing the color composite for fluorescence microscopy images and demonstrating nanoparticle uptake and intracellular drug release at room temperature. Use of identical imaging settings permits direct comparison of fluorescence intensities. Left image: cells not incubated with nanoparticles result in negligible signal. Middle image: cells after 15 minutes incubation with the nanoparticles. Clearly visible is the separation of the PSA-PCL drug carrier (red) and CyA (green) that appears strongly localized at the plasma membrane. Right Image: Cells after 60 minute incubation. Fluorescence signals from PSA-PCL (red) and CyA (green) are much higher indicating much increased nanoparticle uptake. Scale bars are 5 µm.

Figure 9:
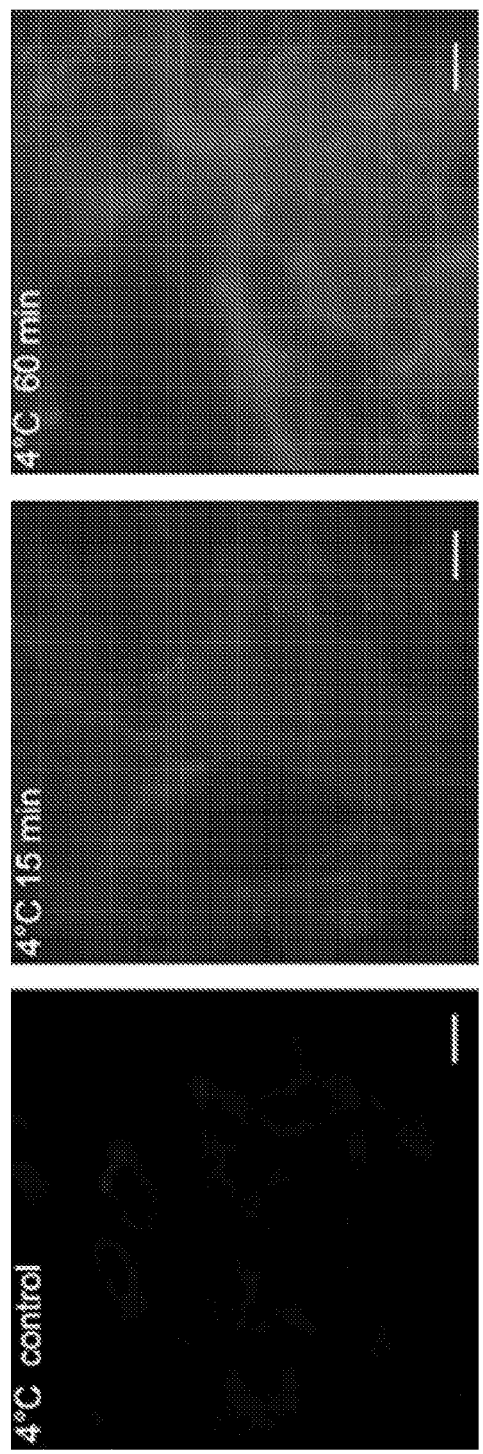

FIG. 9 is a series of micrographs showing the color composite of fluorescence images demonstrating nanoparticle uptake and drug release at 4° C. Acquisition parameters are the same as in FIG. 8, but because of significantly lower intensities different brightness settings had to be chosen. For a direct comparison see Figure S1 and S2 in supporting information. Left image: cells not incubated with nanoparticles result in negligible signals. Middle image: cells after 15 minutes incubation with the nanoparticles. Some uptake and separation of the PSA-PCL drug carrier (red) and CyA (green) is apparent. Right Image: Cells after 60 minute incubation. Fluorescence signals from both PSA-PCL (red) and CyA (green) have increased indicating additional drug-carrier uptake over time. Scale bars are 5 µm.

Figure 10:
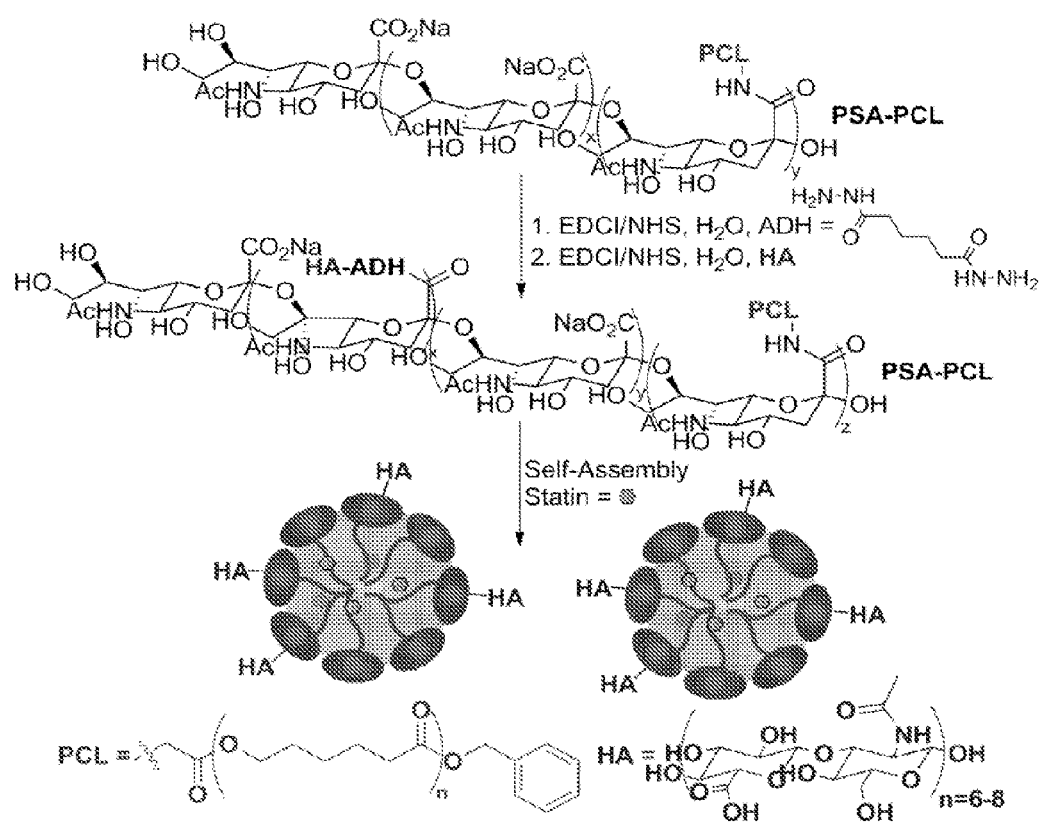

FIG. 10 is a schematic of self-assembled, polysaccharide-based micelle carriers developed by grafting amphiphilic PSA-PCL with HA oligomers.

Figure 11:
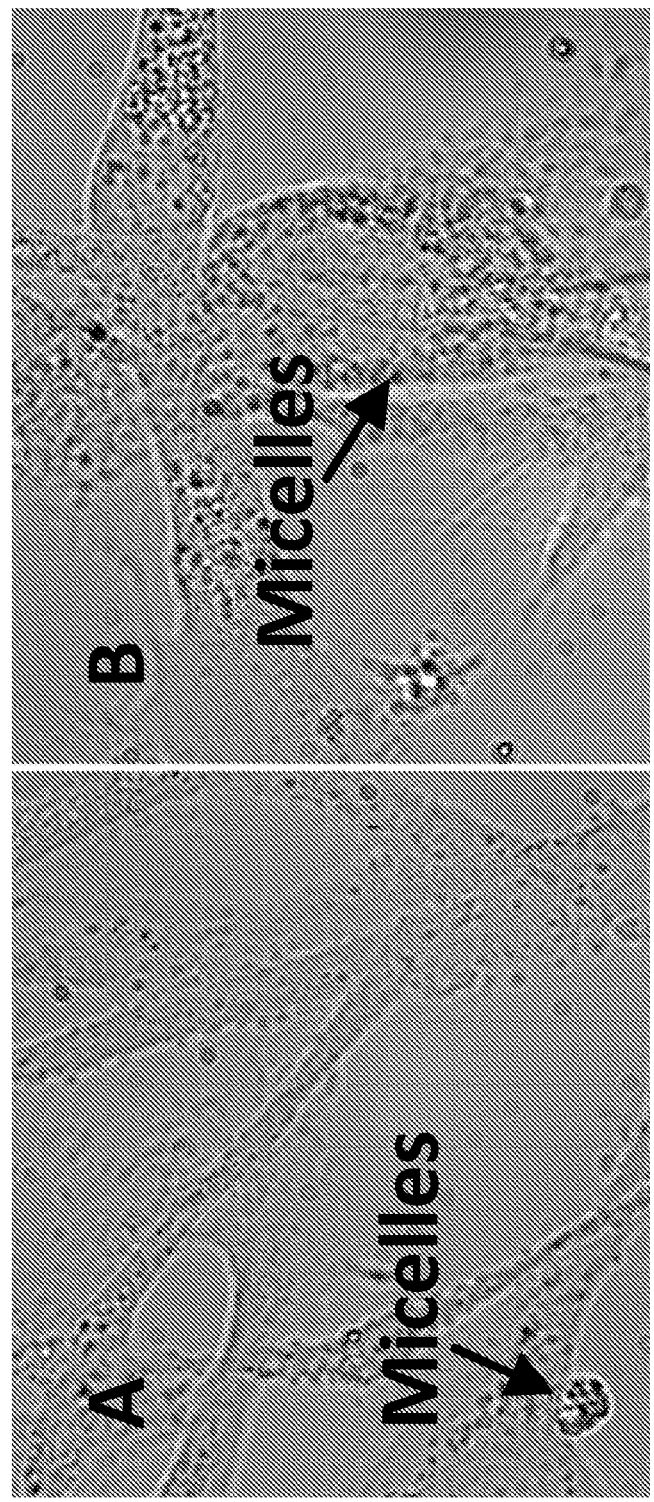

FIG. 11 is a series of micrographs showing cellular uptake of (A) PSA-PCL micelles without HA occurred at a slower rate relative to (B) PSA-PCL-HA micelles.

Figure 12:
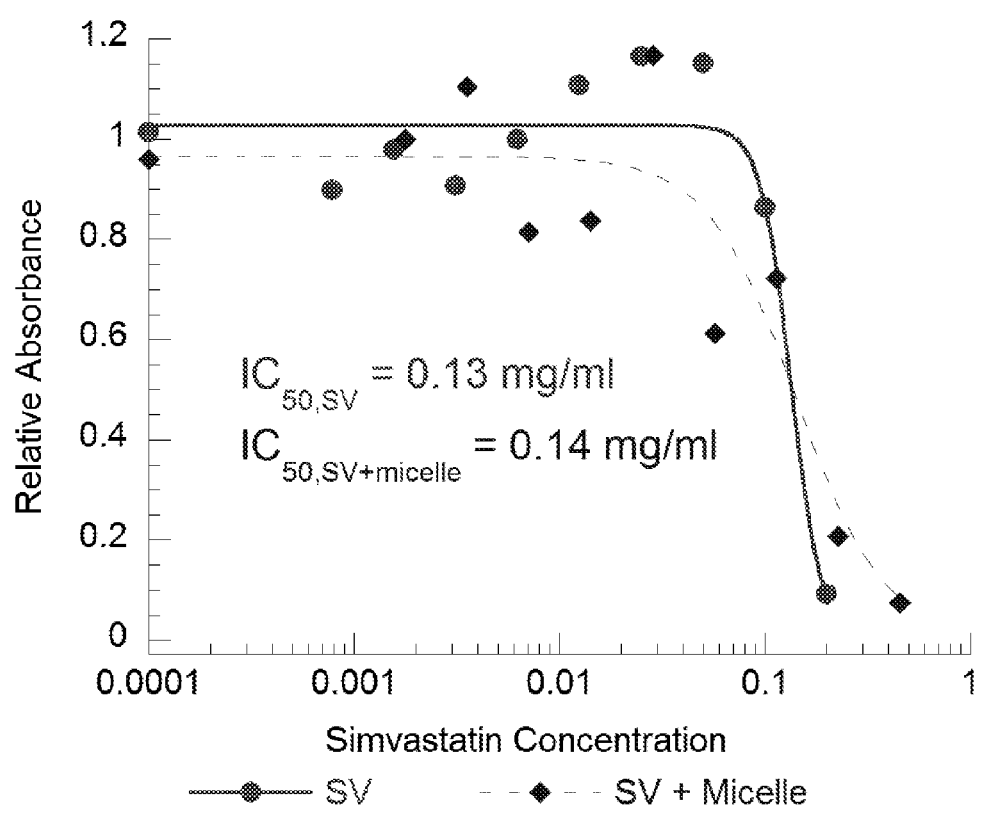

FIG. 12 is a graph of WST-8 assay of IL-1β stimulated VSMCs following incubation with simvastatin (SV) and simvastatin-loaded micelles (SV+Micelle) for 24 h at 37 C over a range of SV concentrations. A hill fit was used to determine the $IC_{50}$ values.

Figure 13:
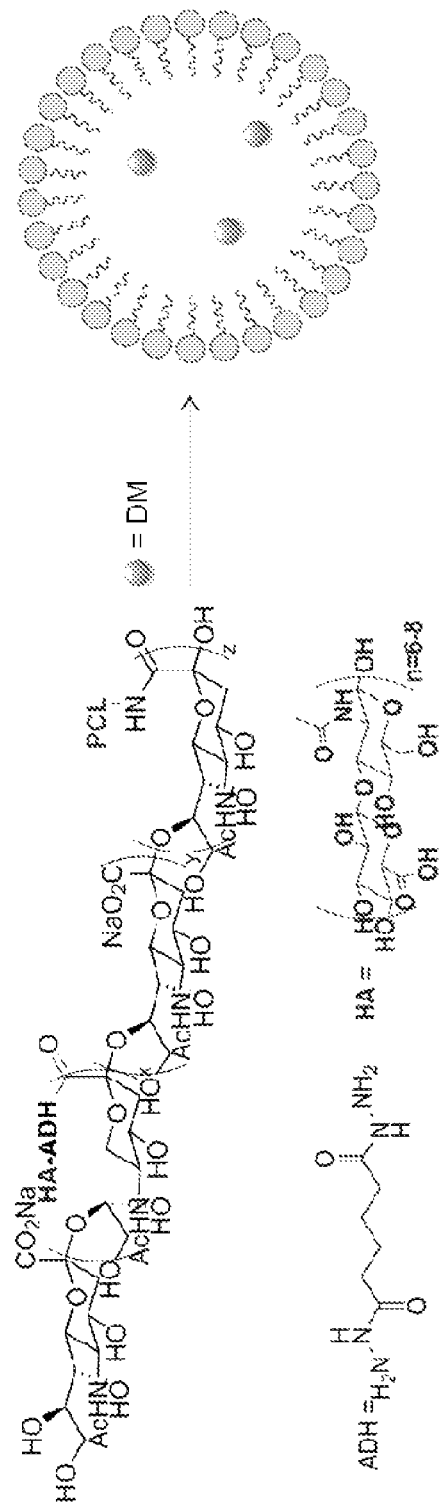

FIG. 13 is a graph of dexamethasone (DM) was entrapped in micelles formed via self-assembly of PSA-PCL modified with HA via an adipic dihydrazide (ADH) tether.

Figure 14:
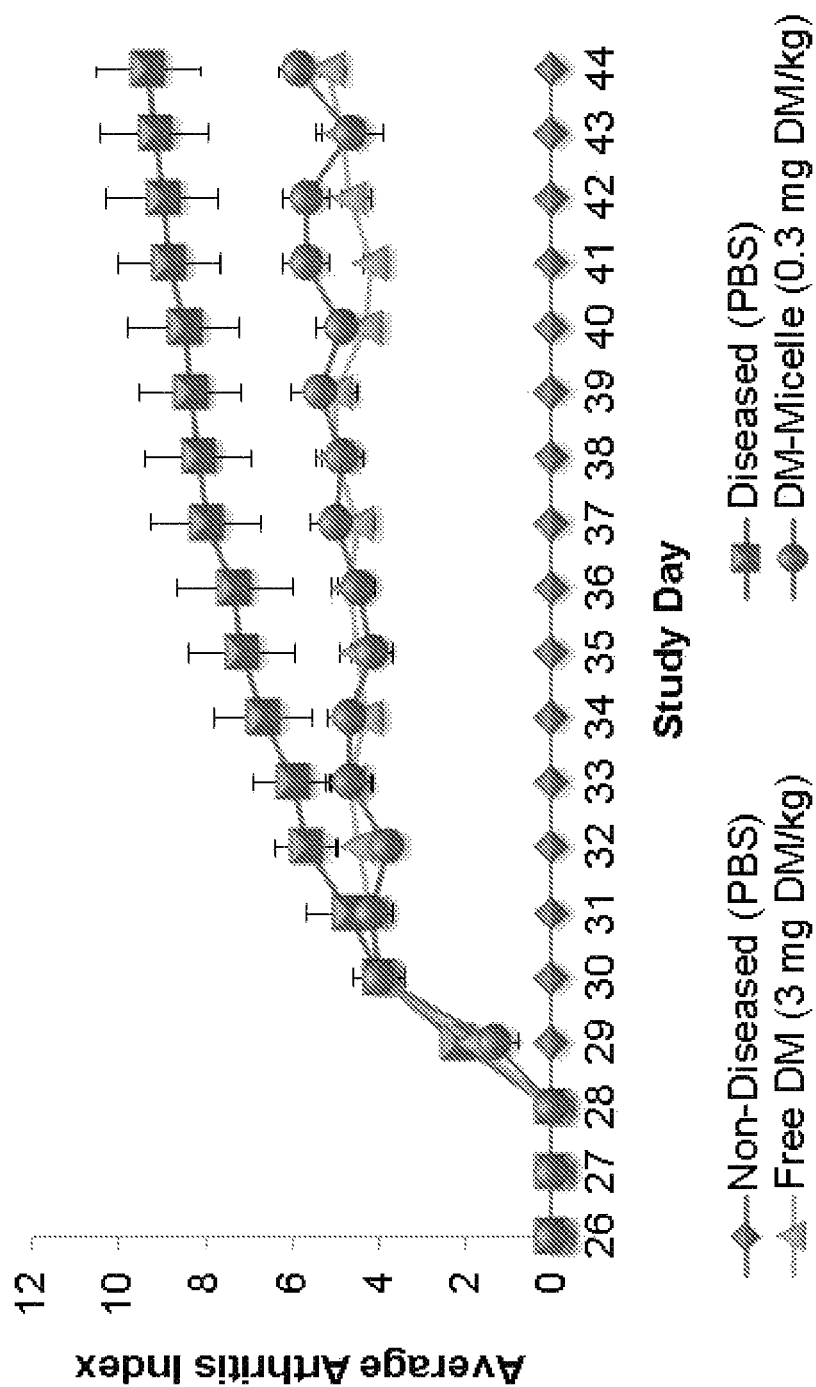

FIG. 14 is a graph of the average arthritis indices of CIA mice treated with DM-loaded micelles were compared to values obtained for mice administered free DM at a ten times higher dose, diseased mice without treatment, and non-diseased mice.

DETAILED DESCRIPTION OF THE INVENTION

Referring now to the drawings, wherein like reference numerals refer to like parts throughout, the present invention comprises PSA-based micelles were formed via self-assembly of PSA grafted with polycaprolactone (PCL) at a critical micelle concentration of 84.7±13.2 µg/ml. Cyclosporine A (CyA), a therapeutic used in the treatment of rheumatoid arthritis, was loaded into the PSA-PCL micelles with a loading capacity and loading efficiency of 0.09±0.02 mg CyA/mg PSA-PCL and 29.3±6.4%, respectively. CyA loading resulted in a size increase from 73.8±12.4 nm to 107.5±9.3 nm at 25° C. and from 138.4±40.7 nm to 195.3±52.1 nm at 37° C., favorable size ranges for drug delivery to inflamed tissue characterized by leaky vasculature, as occurs during rheumatoid arthritis pathogenesis. As an indicator of the stealth nature the micelles are expected to exhibit in vivo, the fixed aqueous layer thickness of the PSA-PCL micelles was determined to be 0.63±0.02 nm, comparable to that obtained for traditionally utilized poly (ethylene glycol) coated liposomes. The PSA-PCL micelles had a negligible effect on the viability of the SW982 synovial fibroblast cell line. Fluorescent microscopy was utilized to demonstrate uptake by the synovial fibroblasts through a nonreceptor mediated form of endocytosis and partitioning of CyA into the membrane. The PSA-PCL micelles also demonstrated therapeutic efficacy in drug delivery when used to deliver statins.

Figure 1:
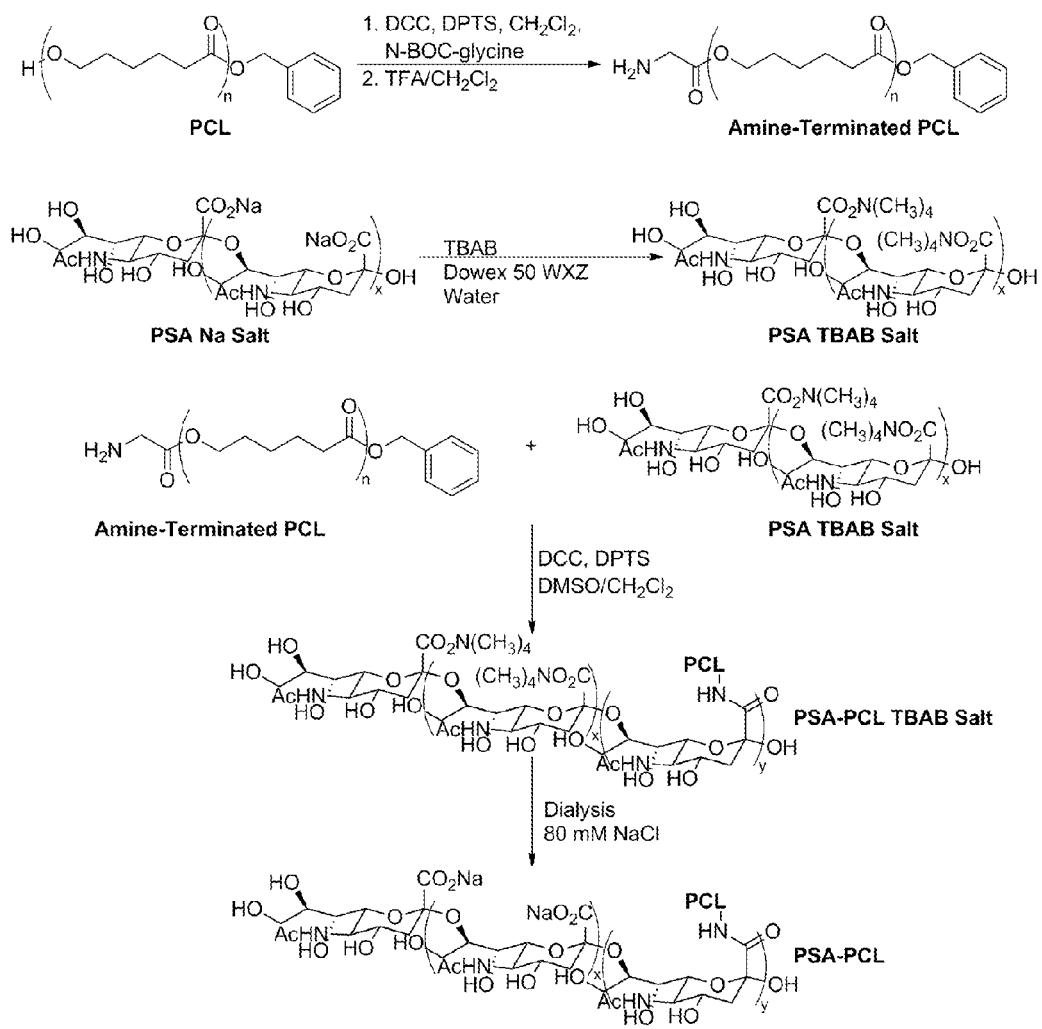
FIG. 1 is a schematic of the synthesis of polysialic acid-polycaprolactone (PSA-PCL) for micelle formation.

As seen in FIG. 1, non-cytotoxic, PSA-based micelles were formed via grafting of the PSA backbone with amine-terminated polycaprolactone (PCL), which is a hydrophobic, non-toxic polymer that can be degraded in the human body by ester hydrolysis. The protective role the PSA is thought to play in vivo was preliminarily evaluated by measurement of the fixed aqueous layer thickness (FALT). FALT has previously been correlated with the ability of carrier systems to prevent opsonization and, consequently, uptake by the reticuloendothelial system (RES). Cyclosporine A (CyA), a therapeutic used in the treatment of rheumatoid arthritis, was used as a model compound to demonstrate the capacity of the micelles to encapsulate hydrophobic molecules. Fluorescence microscopy experiments were used to demonstrate cellular uptake of the drug-loaded micelles and release of the CyA from the micelles.

Example 1

Materials

Colominic acid sodium salt (PSA, isolated from *E. coli*, $M_w$ 30 kDa) was obtained from Nacalai USA (San Diego, Calif.). N-(3-Dimethylaminopropyl)-N'-ethylcarbodiimide (EDCI), N,N'-dicyclohexylcarbodiimide (DCC), N-hydroxysuccinimide (NHS), ethylenediamine, mchloro-peroxybenzoic acid, benzyl alcohol, 1,5,7-triazabicyclo[4.4.0]dec-5-ene (TBD), ε-caprolactone (ε-CL), and Boc-gly-OH were purchased from Sigma-Aldrich (St. Louis, Mo.) and used as received. Trifluoroacetic acid (TFA) (peptide synthesis grade), HPLC grade acetonitrile, dichloromethane, and anhydrous DMSO were also obtained from Sigma-Aldrich. (St. Louis, Mo.). Dichloromethane was distilled before use. Dowex 50WX 2 ion-exchange resin and pyrene were purchased from Acros organics (Pittsburgh, Pa.) and tetrabutylammonium bromide were obtained from Fluka (St. Louis, Mo.). The SW982 synovial fibroblast cell line was acquired from ATCC (Manassas, Va.). Fetal bovine serum (FBS) was obtained from Lonza (Allendale, N.J.) and cyclosporine A (CyA) was purchased from Enzo Life Sciences (Farmingdale, N.Y.). Dulbecco's Modification of Eagle's Medium (DMEM) supplemented with 4.5 g/L glucose, L-glutamine & sodium pyruvate was procured from Mediatech, Inc. (Manassas, Va.). Purified soluble collagen was purchased from Devro Pty Ltd. (Bathurst, NSW, Australia). Alexa Fluor® 488 succinimidyl ester and sulforhodamine 101 cadaverine were acquired from Invitrogen (Grand Island, N.Y.) and AnaSpec (Fremont, Calif.), respectively. 1,2-dipalmitoyl-sn-glycero-3-phosphocholine (DPPC), cholesterol and 1,2-distearoyl-sn-glycero-3-phosphoethanolamine-N-[methoxy(polyethylene glycol)-2000] (DSPE PEG 2000) were obtained from Avanti Polar Lipids (Alabaster, Ala.) and used without further purification. (Dimethylamino)pyridine-p-toluenesulfonic acid (DPTS) was formed from hydrated p-toluenesulfonic acid and 4-(dimethylamino)pyridinium following a known protocol (Moore and Stupp, 1990).

Preparation of Polysialic Acid-Polycaprolactone (PSA-PCL) Micelles

PCL-OH was synthesized according to a published procedure. To a previously incubated solution of benzyl alcohol (5.5 µL, 5.31×10-2 mmol) and TBD (0.04 M in toluene, 3.7 mL, 0.148 mmol), ε-CL (0.82 mL, 7.4 mmol) was added and the mixture was stirred at room temperature, under nitrogen, for 2.5 hr. The polymerization was then quenched by precipitation into cold methanol and PCL-OH was isolated as a colorless oil. Residual catalyst and unreacted monomer were removed from the isolated polymer by repeated precipitation into cold methanol. Polymer formation was confirmed by 1H NMR and gel permeation chromatography in chloroform with polystyrene standards was used to estimate molecular weight (Mw=8216 g/mol).

A two-step process was used to generate PCL-gly-$NH_2$. 200 mg of hydroxyl-terminated PCL. (026 mmol), 5.5 mg DCC (0.026 mmol), and 14.6 mg DPTS (0.026 mmol) were dissolved in 6 ml anhydrous dichloromethane under nitrogen, and 4.6 mg BOCglycine (0.026 mmol) were added. The reaction solution was stirred for 48 h at room temperature. After filtration, the solution was added drop-wise into 30 ml of cold methanol. The white precipitate was collected and dried in a vacuum oven overnight. The resultant 141.1 mg of PCL-gly-Boc (Mw=8374 g/mol, ~0.017 mmol) was dissolved in 7 ml anhydrous dichloromethane and 7 ml of TFA was added via syringe. The mixture was stirred at room temperature for 2 h under nitrogen. The product was obtained by rotary evaporation followed by drying at 70° C. in a vacuum oven. Formation of PCL-gly-Boc and deprotection to yield PCL-gly-$NH_2$ were confirmed by 1H NMR (300 MHz, CD3Cl).

To improve the solubility of PSA in DMSO, the sodium ion was exchanged for tetrabutylammonium using a procedure adapted from the literature. 600 mg Dowex 50 WXZ and 750 mg tetrabutylammonium bromide (2.26 mmol) were mixed in 15 ml of DI water, and the mixture was stirred gently for 1 hour. The Dowex 50 WXZ was washed several times with DI water to remove unbound tetrabutylammonium bromide. The washed Dowex was transferred into 10 ml of 2% aqueous (w/w) PSA (200 mg, 0.65 mmol sialic acid monomer), and the solution stirred for 2 hours at room temperature. The resin was separated from the liquid by centrifugation at 1000 rpm for 5 min. Ion exchanged PSA was isolated via lyophilization.

To conjugate PCL-gly-$NH_2$ to PSA, 100 mg of ion exchanged PSA (0.32 mmol sialic acid monomer), 10.1 mg DCC (0.048 mmol, 0.15 equiv relative to sialic acid monomer), and 26.8 mg DPTS (0.048 mmol, 0.15 equiv) were combined in 6 ml of anhydrous DMSO, and the solution was stirred for 1 h at room temperature under nitrogen. Simultaneously, 133 mg PCLgly-$NH_2$ (0.016 mmol, 0.05 equiv) were dissolved in 6 ml anhydrous dichloromethane in a separate round bottom flask. After 1 hour, the dichloromethane solution was transferred to the DMSO solution via cannula. The mixture was allowed to stir overnight at room temperature. After filtration, the solution was dialyzed against 150 mM NaCl solution overnight to remove solvent and exchange tetrabutylammonium for sodium. Residual dichloromethane was removed by rotary evaporation, and the product was isolated by lyophilization. The resultant powder was dissolved in DI water, filtered to ensure removal of unreacted PCL-gly-$NH_2$, and re-lyophilized to obtain the final product. The formation of PSA-PCL was confirmed by 1H NMR. The degree of substitution (DS) of PCL to sialic acid monomer found by $$DS = \left(\frac{3}{2}\right)\left(\frac{A1.35}{A2.1}\right)\left(\frac{M_W PCL}{M_W \varepsilon\text{-}CL}\right) \quad (1)$$

where A1.35 and A2.1 are the peak areas at δ 1.35 and 2.1 ppm, respectively.

CMC was evaluated via steady-state fluorescence using pyrene as a probe. 8.1 µL of a 1.24×10-4 M pyrene stock solution in acetone was added to nine individual vials, and the acetone was allowed to evaporate by placing on a 65° C. hot plate for 15 min. Simultaneously, a dilution series of aqueous PSA-PCL solutions with concentrations ranging from 1 mg/ml to 3.9 µg/ml was prepared. 1 ml of the aqueous micelle solutions was added to the nine vials with pyrene. The solutions were sonicated for 30 min at room temperature and heated with shaking at 65° C. for 4 h to achieve equilibration. After cooling in the dark overnight, excitation spectra were recorded at an emission wavelength of 390 nm with a QuantaMaster-4/2005 sensitivity enhanced (QM-4/2005 SE, Photon Technology International) fluorescence spectrophotometer.

Size, polydispersity, and zeta potential of PSA-PCL micelles, with and without encapsulated CyA, were obtained with a Zetasizer Nano ZS (Malvern Instruments). Aqueous samples were prepared by dissolving 1 mg PSA-PCL in 1 ml DI water. For dynamic light scattering, the temperature for measurement was 25° C., and the angle of scattered light was 173°. Micelle sizes are reported as the mean of the sizes derived from the number distributions plus/minus the standard deviation, while size distributions are reported as the mean of the polydispersity indices (PDIs) plus/minus the standard deviation. To verify that micelles were formed at concentrations approaching the CMC and to establish physiological stability, size measurements were also made at concentrations of 0.1 and 10 mg/ml and at 37° C.

Lyophilized PSA-PCL was dissolved in DI water at a concentration of 0.1 mg/ml to facilitate self-assembly of micelles. 20 µl of the PSA-PCL micelle solution was pipetted onto a formvar/carbon coated copper grid (Electron Microscopy Sciences, Inc.). The excess micelle solution was removed, and the sample was stained with methylamine vanadate prior to imaging with a JEOL 2000EX TEM at 100 kV at the N.C. Brown Center for Ultrastructure Studies at the SUNY College of Environmental Science and Forestry.

Cytotoxicity of PSA-PCL was evaluated via WST-8 assay (Cayman Chemical Company, Ann Arbor, Mich.) using the SW892 synovial fibroblast cell line. Cells were seeded into a 96-well plate at a density of 10,000 per well and cultured for 24 h with DMEM plus 10% FBS at 37° C., 5% CO2. Following sterile filtration, PSA-PCL micelles were added at concentrations ranging from 0.156-20 mg/ml. After incubating for 24 h, the media was removed and 10 µl of WST-8 reagent and 100 µl of fresh media were added to each well. After a 90 min incubation period, the absorbance was measured at 450 nm by a Synergy 2 multimode microplate reader (Biotek Instruments). SW982 cells cultured without PSA-PCL were used as controls. The experiment was repeated independently three times. IC50 concentrations were determined from a four parameter logistic generated using Kaleidagraph software.

CyA was encapsulated using a previously established approach. 1.5 mg of CyA was dissolved in 4 ml of a 1:1 mixture of methanol and DMSO. 10 mg of PSA-PCL were added. To initiate micelle formation, 1 ml of DI water was added. The solution was transferred to a dialysis membrane (Spectrum Laboratories, Inc., MWCO=6-8 kDa) and dialyzed against DI water for 2 days to remove organic solvent and facilitate self-assembly with entrapped CyA. Loading capacity (LC) and loading efficiency (LE) of the CyA-loaded PSA-PCL micelles were assessed with a Prominence Ultrafast Liquid Chromatography System (UFLC, Shimadzu Scientific Instruments, Japan) equipped with an SPD-20AV UV detector, an SIL-20A autosampler, an DGU-20A3 degasser, and a Shim-pack XRODS/C8/Phenyl column (3 mm i.d.×50 mm). 10 mg of lyophilized, CyA-loaded PSA-PCL was dissolved in 4 ml of mobile phase, a 65:35 mixture (v/v) of pure HPLC grade acetonitrile and DI water, and mixed well. All samples were filtered through 0.25 µm filter prior to injection. An injection volume of 100 µL was used, and the flow rate and detection wavelength were set to 210 nm and 0.5 ml/min, respectively. At a column temperature of 40° C., CyA was observed as a broad peak centered at an elution time of 8.3 min. A calibration curve was constructed by determining the area under the peak using PeakFit 4.2 software for eight CyA solutions with known concentrations ranging from 50 to 400 µg/ml. Samples of CyA-loaded micelles were diluted with acetonitrile to release encapsulated drug (65 acetonitrile:35 water). LC and LE were determined as:

$$LC = \frac{W_{CyA\text{-}loaded}}{W_{PSA\text{-}PCL}} \quad (2)$$

$$LE = \frac{W_{CyA\text{-}loaded}}{W_{CyA\text{-}added}} \quad (3)$$

where $W_{CyA\text{-}loaded}$ is the amount of CyA incorporated into the micelles, as determined using the calibration curve, and $W_{PSA\text{-}PCL}$ and $W_{CyA\text{-}added}$ are the amounts of PSA-PCL and CyA used, respectively.

To assess the feasibility of long-term storage, CyA-loaded PCL micelles, prepared as described above, were frozen in a −80° C. freezer without the addition of a stabilizer and lyophilized with a freeze-dryer. Reconstituted samples were prepared by adding DI water and briefly vortexing. After centrifugation at 3000 g for 5 min to remove any CyA that was released during the freeze drying process, the micelle solutions were characterized by dynamic light scattering and UFLC.

To assess mechanical stability, samples of CyA-loaded PSA-PCL micelles samples were centrifuged at 11000 g for 5 min. To LC=WCyA-loaded WPSA-PCL LE=WCyA-loaded WCyA-added evaluate thermal stability, the samples were incubated at 37° C. with gentle shaking for 1 week. At the end of the thermal stability tests, free CyA was removed by centrifugation at 3000 rpm for 5 min. After separation from the CyA pellet, the micelle solutions from the mechanical and thermal stability tests were characterized by dynamic light scattering at 37° C. and UFLC. Each stability test was repeated three times.

Small unilamellar vesicles of average diameter of 100 nm composed of 62 mol % DPPC, 33 mol % cholesterol and 5 mol % DSPE-PEG 2000 were prepared by the vesicle extrusion methods. In brief, the lipids were suspended in chloroform and mixed in a round bottom glass vial. The solvent was evaporated, and the dried lipid film was resuspended with double-deionized water and hydrated overnight at 4° C. The total lipid concentration was 2 mg/ml. The liposomes were homogenized by passing them with 1800 kPa 11 times through polycarbonate filters of 100 nm pore diameter (Whatman Inc., Clifton, N.J.) using a high pressure extruder (Northern Lipids Inc., Vancouver, Canada).

The FALTs of PSA-PCL micelles and PEG-coated liposomes were determined following a previously described method based on the Gouy-Chapman theory. Zeta potentials for micelles and PEG-coated liposomes were obtained in the following concentrations of aqueous NaCl: 10, 50, 100, 150, and 200 mM. Using eq. 1, FALT was estimated from a plot of zeta potential (ψ) versus the Debye-Huckel parameter (κ=√(C/0.3), where C is the molarity of NaCl).

To facilitate attachment of a fluorescent tag, a CyA analog with a reactive functional group was prepared. The procedure outlined herein for the preparation of CyA-NH$_2$ was adapted from a previous study on the synthesis of cyclosporine A derivatives. Briefly, 200 mg CyA (166 μmol), 32 mg m-chloro-peroxybenzoic acid (186 μmol), and 40 mg anhydrous sodium carbonate (380 μmol) were combined in 20 ml of anhydrous methylene chloride, and the reaction solution was stirred overnight under N2 at room temperature. The solution was washed with 20% sodium bisulfite and 10% sodium carbonate. The organic layer was dried over anhydrous magnesium sulfate, filtered, and concentrated to yield 190 mg of crystalline product. This was immediately dissolved in 20 ml of anhydrous THF and refluxed under N2 with excess ethylenediamine (400 μl, 359.6 mg, 5.98 mmol) for 24 h at 80° C. The solution was concentrated, and flash chromatography on silica gel (SiliaFlash® F60) was used to isolate the product. The colorless byproduct was eluted first with hexane/acetone (1:2), and then methanol/dichloromethane (4:1) was used to obtain the product as a yellow residue. Product formation was confirmed by high resolution electrospray ionization mass spectrometry on a Bruker 12 Tesla APEX-Qe FTICR-MS with an Apollo II ion source at the COSMIC laboratory of Old Dominion University. HRMS calculated for CyA-NH$_2$ [M+Na]+ 1300.8942. Found 1300.8904.

Fluorescently labeled CyA was synthesized by dissolving 12 mg of CyA-NH$_2$ (9.22 μmol) in 1 ml DMSO, followed by the addition of 250 μl (0.25 mg, 0.39 μmol) Alexa Fluor® 488 carboxylic acid, succinimidyl ester, mixed isomers in DMSO. The solution was stirred for 2 h with protection from light at room temperature and then dialyzed against DI water using a Spectra/Por® Float-A-Lyzer® G2 device (Spectrum Laboratories, Inc., MWCO=0.5-1.0 kDa) overnight to remove unreacted fluorescence tag. Due to the excess of CyA-NH$_2$ relative to Alexa Fluor 488 (~24 fold), the amount of unreacted tag is presumed to be negligible. Fluorescently labeled CyA was isolated by lyophilization, and conjugation of the fluorescent moiety to CyA was verified by 1H NMR. Fluorescently labeled PSA-PCL was prepared by dissolving 40 mg of PSA-PCL (~97 μmol sialic acid monomer) in 4 ml of DI water, followed by the addition of 15.5 mg EDCI (99.9 μmol), 11.5 mg NHS (99.9 μmol) and 400 μl sulforhodamine 101 cadaverine (1 mg, 1.45 μmol). The pH was adjusted to 4.75, and the solution was stirred overnight with protection from light at room temperature. Unreacted fluorescent tag was removed by dialysis against DI water overnight using standard dialysis tubing (Spectrum Laboratories, Inc., MWCO=6-8 kDa).

Fluorescently labeled PSA-PCL was isolated by lyophilization, and attachment of the fluorescent tag to PSAPCL was confirmed by 1H NMR. Self-assembly of the fluorescently-labeled PSA-PCL into micelles was demonstrated via dynamic light scattering. Fluorescently-labeled CyA was encapsulated within fluorescently-labeled PSA-PCL as described above for un-labeled material. Dialysis against 1xPBS (Spectrum Laboratories, Inc., MWCO=6-8 kDa) yielded a solution that was used immediately for cellular uptake experiments. The large molecular weight cut off of the dialysis membrane further ensures removal of unreacted, water soluble Alexa Fluor® 488.

Quantitative fluorescence imaging of cellular uptake 35 mm Glass-bottom dishes (MatTek, Ashland, Mass.) were coated with collagen prior to use to improve cell viability and morphology. Collagen was dissolved in 0.02 M acetic acid at a concentration of 50 μg/ml, and 1 ml of the resultant solution was sterile filtered and added to each microscopy plate. After 1 h at room temperature, excess collagen solution was removed by gentle aspiration, and the plates were rinsed 3 times with 1xPBS. The plates were air dried overnight inside a biosafety cabinet.

SW982 cells were seeded into the collagen-coated plates at a density 1 million cells/plate. After 24 h of incubation at 37° C., the media was removed and sterile filtered fluorescently labeled CyA-loaded PSA-PSA micelle solution was added, The plates were washed 3 times with 1xPBS before imaging, and images were obtained with a Nikon Eclipse Ti inverted microscope at 15 and 60 min post-administration using a Xion 888 (Andor Technology plc., Belfast, UK). Experiments were conducted at both room temperature and 4 degrees in order to garner a better understanding of the uptake mechanism. To quantitatively compare images all illumination and acquisition parameters for the 16 bit monochrome images were kept constant. In addition, identical image processing routines were used for all images at one temperature in post processing utilizing at most linear transformations. While this prevents optimization of contrast and image fidelity for every image, direct and quantitative comparison between images at one temperature are allowed. However, since the fluorescence intensities span as much as 3 orders of magnitude, the same post processing for all images could not be used across different temperatures. The latter fact and the resultant consequences are further discussed and illustrated in the supplemental materials.

PSA-PCL was successfully synthesized via amide bond formation between PSA and amine-terminated PCL. Low molecular weight PCL (Mw~8000) was synthesized via dual activation of the benzyl alcohol initiator and ε-caprolactone monomer with 1,5,7-triazabicyclo[4.4.0]dec-5-ene (TBD) catalyst. The terminal hydroxyl group of the PCL polymer was subsequently conjugated to Boc-protected glycine. Acid catalyzed deprotection yielded the desired amine-terminated PCL. To facilitate the reaction between organic soluble PCL and water soluble PSA, the counterion of PSA was exchanged from sodium to tetrabutylammonium. Following PSA-PCL conjugation in a mixture of methylene chloride and DMSO, the ion was changed back to sodium by dialyzing the product against 150 mM aqueous NaCl for 2 days. The latter step was necessary to prevent potential toxicity from the tetrabutylammonium salt. From 1H NMR, the degree of substitution, defined as the percentage of monomers on the PSA backbone grafted with PCL, was determined to be approximately 1%, or a weight ratio of 4 PSA:1 PCL.

Figure 2:
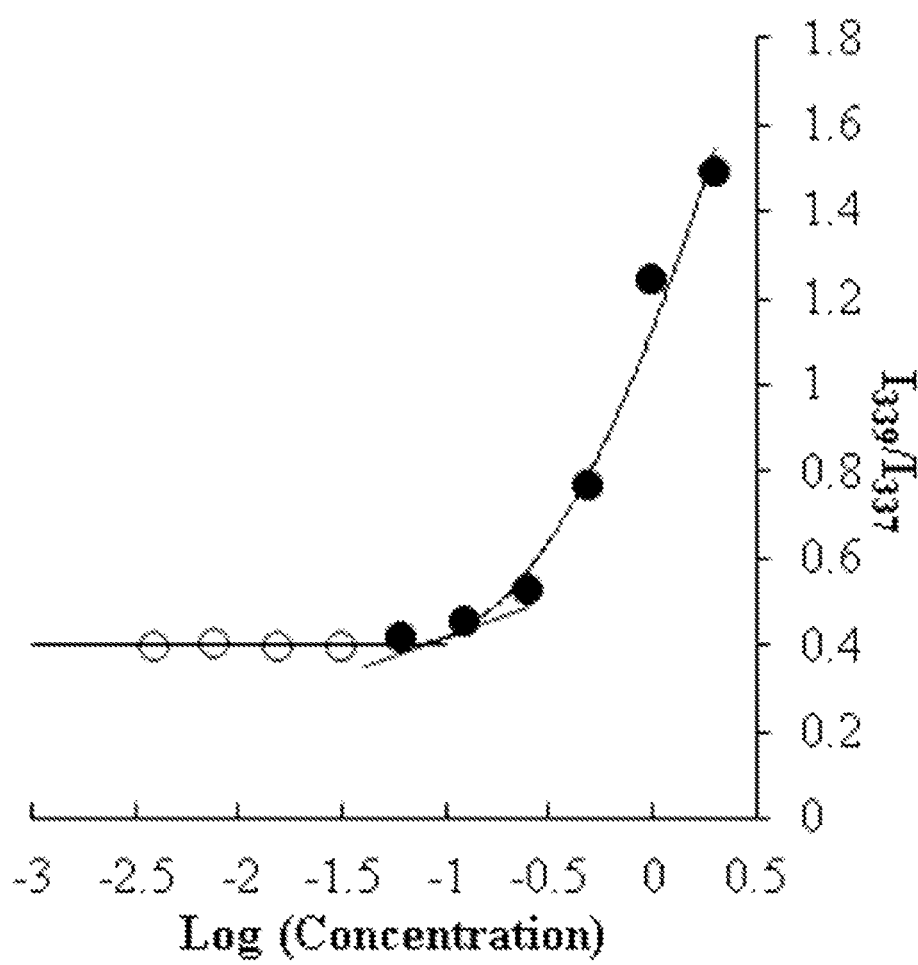
FIG. 2 is a representative plot showing the change in 1339/1337 for pyrene as the concentration of PSA-PCL (mg/mL) is increased. The critical micelle concentration was identified as 84.7±13.2 µg/ml from the intersection of the tangent of the inflection point with the horizontal tangent of the low concentration points.

The capacity for PSA-PCL to self-assemble into micelles was assessed using pyrene as a fluorescent probe based upon established methodology. As the PSA-PCL concentration was increased past that required for micelle formation, i.e. the critical micelle concentration (CMC), the pyrene achieved a new equilibrium between the hydrophobic core of the micelle and the hydrophilic aqueous solution. These changes in the distribution between the hydrophilic and the hydrophobic phases resulted in a measurable shift in the pyrene excitation spectrum. By plotting the ratio of intensities at 339 and 337 nm (emission wavelength=390 nm), as a function of the log of PSA-PCL concentration, the CMC was determined to be 84.7±13.2 μg/ml from the intersection of the tangent of the inflection point with the horizontal tangent of the low concentration points, as seen in FIG. 2. The low value obtained for PSA-PCL is consistent with the CMC of decylamine-modified PSA and other polysaccharides based micelle systems. Of note, the pyrene method was chosen over other potential approaches, such as surface tension and DPH, to ensure the accuracy of the established CMC value. Determination of CMC by surface tension is complex, time consuming, and is potentially sensitive to impurities; thus, this approach does not always provide reliable values. Likewise, the shift in fluorescence characteristics of 1,6-Diphenyl-1,3,5-hexatriene (DPH) with increasing concentration of the amphiphilic system does not always facilitate identification of an accurate CMC.

The size of the PSA-PCL micelles without encapsulated therapeutics at a concentration of 1 mg/ml at room and physiological temperature was 73.8±13.4 nm and 138.4±40.7 nm, respectively, as determined by dynamic light scattering and confirmed by transmission electron microscopy, as seen in FIGS. 3 and 4. As expected, the size and distribution of the micelles increased upon dilution to a concentration near that of the CMC, particularly at 37° C., as seen in FIG. 3. In subsequent studies, the impact of dilution on micelle size and stability may be further explored, with and without encapsulated therapeutics, and in the presence and absence of serum proteins. However, based on the initial size measurements alone, PSA-PCL micelles are suitable for use as part of a treatment strategy. In drug delivery, particle size has a known significant impact on drug distribution, excretion, and efficacy. Microparticles primarily accumulate in the lungs, while larger nanoparticles (>200 nm) are usually trapped and eliminated quickly by reticuloendothelial system (RES). In contrast, if the size is under 10 nm, the particles are often rapidly excreted by the kidneys. Therefore, the particles intended for long circulation should ideally possess a size between 10 and 200 nm, as was obtained here. Moreover, inflamed tissue, such as that found in rheumatoid arthritis, has poorly organized vascular structure due to angiogenesis, immune cell accumulation, and an imbalance in the secretion of signaling molecules. Nanoparticles with sufficient size to evade kidney filtration, but small enough to avoid RES uptake, will passively accumulate within inflamed tissues.

To provide an initial assessment of the surface properties, the zeta potential of the PSAPCL micelles was determined to be −29.7±8.0. As empirically established, an absolute value between 30-40 mV indicates a stable colloidal particle system, while a negative zeta potential reduces particle interaction with negatively charged serum proteins. Thus, initial size and surface charge measurements suggest that PSA-PCL micelle may serve as effective carrier system. As discussed below, to obtain a better sense of surface properties, zeta potential measurements were also used in conjunction with Guoy-Chapman theory to assess the fixed aqueous layer thickness (FALT).

Cytotoxicity was assessed using the SW982 human synovial sarcoma cell line via WST-8 assay. The cell line was chosen based upon future in vitro tests that will be used to assess the efficacy of CyA-loaded PSA-PCL micelles in the treatment of rheumatoid arthritis. As seen in FIG. 5, the $IC_{50}$ for PSA-PCL was determined to be 10.5±1.7 mg/ml, a value greater than or comparable to other polymeric micelle systems that are considered to be noncytotoxic. In addition, the $IC_{50}$ value obtained here was significantly greater than that obtained previously for micelles prepared from polysialic acid modified with short chain hydrocarbons. The lack of observed cytotoxicity provides an indicator of biocompatibility for subsequent in vivo experiments. Notably, CyA has previously been shown to be non-cytotoxic towards human synovial fibroblasts.

CyA was chosen as a representative drug to evaluate the potential of PSA-PCL as a carrier system for use in the treatment of rheumatoid arthritis. CyA is a regularly used disease modifying anti-rheumatic drug with strong immunosuppressive properties. Despite a demonstrated ability to alter the progression of rheumatoid arthritis in many patients, CyA is nephrotoxic; therefore, frequent monitoring for signs of possible renal dysfunction and kidney damage is necessary. In part, the observed toxicity is likely a consequence of the large, between-patient variability in pharmacokinetic parameters. Thus, CyA is an ideal candidate for incorporation into a drug delivery system that will serve to improve the pharmacokinetic profile.

The therapeutic efficacy of CyA is primarily attributed to inhibition of T cell activation; however, CyA has also been shown to reduce the expression/secretion of proinflammatory cytokines, adhesion molecules, metalloproteinases, and angiogenic growth factors by several other cell types associated with rheumatoid arthritis, particularly synovial fibroblasts. The mechanism by which CyA acts in rheumatoid arthritis and other pathologies has not been fully elucidated. Although numerous studies have demonstrated the interference of CyA with calcium dependent signaling pathways, initial activity has been postulated to be due to partitioning of the hydrophobic drug into the phospholipid membrane and subsequent alteration of phospholipid metabolism. As will be discussed further below, a fluorescently tagged CyA derivative was used in this study to allow for visualization of CyA partitioning to the membrane following administration of the drug-loaded micelles.

An established dialysis method was used to facilitate loading of CyA into the PSA-PCL micelles. A solution of CyA and PSA-PCL in a mixture of methanol, DMSO, and water was extensively dialyzed against water until drug-loaded micelles were formed and most of the residual organic solvent within the dialysis tubing was removed. After dialysis, nonencapsulated CyA was removed by centrifugation, and the drug-loaded micelles characterized immediately or were isolated for storage as a white powder via lyophilization. Size measurements following re-dispersion in water verified that the CyA-loaded PSA-PCL micelles were stable to freeze drying without the addition of a stabilizer, as seen in FIG. 6, as is typically required for PEG-modified systems. The size of the micelles increased to 107.5±9.3 nm and 195.3±52.1 nm upon CyA loading at 25° C. and 37° C., respectively; however, the PDI was significantly lowered from 0.28±0.05 to 0.16±0.01 at 25° C. and 0.19±0.06 to 0.08±0.12 at 37° C., suggesting that the interaction of the PCL with the CyA enhances the stability of the micelles.

CyA encapsulation was quantified by ultrafast liquid chromatography. The loading capacity and loading efficiency were determined to be of 0.09±0.02 mg CyA/mg PSA-PCL and 29.3±6.4%, respectively. Of note, these values were significantly higher than those obtained for a previously developed polysialic-acid based micelle system that utilized short chain hydrocarbons to initiate self-assembly. Presumably, the large, hydrophobic CyA molecules have more favorable interactions with the long hydrophobic chains of PCL relative to the short chain hydrocarbons. The latter result correlates with the observed reduction in the PDI. Moreover, these values were comparable to those obtained by other researchers for drug-loaded polymeric micelle systems. Lyophilization and reconstitution of CyA-loaded PSA-PCL micelles yielded only a small reduction in the amount of encapsulated CyA to 83.7±9.5% of the original amount as see in FIG. 6.

As a preliminary examination of CyA-loaded PSA-PCL micelle stability, changes in size at 37° C. and the percentage of encapsulated drug following thermal and mechanical testing were assessed. Micelle size, as seen in FIG. 6, and distribution were not significantly impacted by high speed centrifugation or by incubation at 37° C. with gentle shaking for 1 week, although there was a trend towards smaller sizes with the latter test. The smaller size of the micelles subjected to prolonged incubation at 37° C. correlates with the observed reduction in encapsulated CyA to 54.4±2.2% of the original amount. Taken in conjunction with observations from the cellular uptake experiments described below, the high retention of CyA by the micelles at physiological temperature suggests that targeted delivery with primarily intracellular release is feasible. High speed centrifugation only led to a decrease in encapsulated CyA to 85.0±2.1% of the original amount, as seen in FIG. 6. Additional in vitro tests on physiological stability and therapeutic efficacy, including evaluation of the ability of PSA-based micelles to prevent binding of serum proteins, will be the topic of subsequent investigations. 3.3. Comparison of PSA-PCL micelles to PEG-coated micelles.

PEG modification has long been used as a method to reduce undesirable interactions with the RES and extend the circulation time of drug delivery systems. One of the proposed mechanisms by which PEG modification gives this so-called stealth nature to drug delivery systems, particularly liposomes, is via an increased affinity to water molecule. Thus, several researchers have begun using the fixed aqueous layer thickness (FALT) as a quantitative measure of the ability of colloidal carriers to resist opsonization and subsequent uptake by the RES.

To measure the FALT, the PSA-PCL micelles were suspended in aqueous solution with increasing NaCl concentrations, and the zeta potentials were measured. Assuming a spherical particle and a homogeneous charge distribution, Guoy Chapman theory can be applied to give the zeta potentially $\psi(L)$ as a function of the Debye Huckel parameter, $\kappa = C^{1/2}/0.3$:

$$\text{Ln } \psi(L) = \text{Ln } A - \kappa L \quad (4)$$

where C is the molarity of the NaCl and A is a constant. Plotting Ln $\psi(L)$ versus $\kappa$ yields a straight line with a slope L, equal to the thickness of the FALT in nm. From eq. 1, the FALT for the PSA-based micelles was calculated to be 0.63±0.03 nm. For comparison, traditional, PEG coated liposomes were also prepared, and the FALT was determined to be 0.77±0.11 nm. The comparable values (p>0.05) obtained for the PSA-PCl micelles and PEG-coated liposomes suggest that PSA can provide a similar aqueous layer compared to that afforded by PEG. Furthermore, the FALT of the PSA-PCL micelles was greater than and near those reported in the literature for unmodified liposomes and liposomes coated with low molecular weight PEG, respectively. Of note, PEG-PCL micelles were reported to possess a FALT of 4.32 nm. To verify the latter value, micelles were prepared from commercially available PEG-PCL (Sigma Aldrich. Although the sizes and zeta potential values at 0 mM NaCl were similar, a plot of Ln $\psi(L)$ versus k failed to yield a straight line, suggesting that the assumptions necessary for the Guoy Chapman theory cannot be applied.

To facilitate visualization of micelle uptake and therapeutic release in vitro, the PSA-PCL micelles and CyA were labeled with red (sulforhodamine) and green (Alexa Fluor 488) fluorescent tags, respectively, as seen in FIG. 7. Dynamic light scattering was used to verify that the labeling moiety did not have a significant impact on the size of the PSA-PCL micelles. As expected based upon the low ratio of fluorescent dye to reactive sialic acid groups, addition of sulforhodamine gave micelles with a size of 73.0±5.6 nm, an insignificant difference compared to the size determined for unlabeled PSA-PCL micelles (73.8±13.4 nm).

As shown in FIG. 8, the SW982 cells showed time-dependent uptake of the CyA-loaded micelles, as well as partitioning of the drug into the membrane. The observed presence of CyA within the membrane lends support to the notion that the immunosuppressive activity of CyA is, in part, a result of phospholipid bilayer disruption. Purportedly, changes in membrane organization and fluidity following interactions with CyA yield a reduction in phospholipid metabolism that inhibits cellular activation. An identical set of experiments was conducted at 4° C., rather than room temperature, to preliminarily assess the mechanism of cellular uptake, as seen in FIG. 9. The significant reduction in fluorescence intensity suggests that internalization of the micelles is primarily through energy-dependent endocytic pathways. Of note, rheumatoid arthritis synovial fibroblasts exhibit enhanced endocytic activity compared to healthy synovial fibroblasts. This characteristic is expected to further enhance the targeting ability of carrier systems that enter cells via energy-dependent pathways, including the PSA-PCL micelles.

Example 2

The PSA-PCL micelles of the present invention were also used to deliver statin drugs and demonstrate stable micelle delivery systems that target VSMCs and the ability to load these micelles with statins. The present invention was shown to produce in vitro and in vivo changes in VSMCs and IH, respectively, on statin administration.

Micelles were formed via self-assembly of hydrophilic polysialic acid with hydrophobic polycaprolactone (PSA-PCL) as seen in FIG. 10. Dynamic light scattering and transmission electron microscopy validated formation of stable micelles with a size of ~100 nm and low polydispersity. To facilitate active targeting of the CD44 HA (hyaluronic acid) receptor that is upregulated on VSMCs upon balloon injury, HA oligomer agonists were attached to a small percentage (<1%) of the PSA monomers of PSA-PCL through an adipic dihydrazide (ADH) tether. The choice to use HA oligomers as targeting groups was based upon prior success by others at targeting the overexpressed CD44 receptor of various cell types, in combination with evidence demonstrating the abundance of the CD44 receptor on VSMCs following balloon angioplasty in a rat model. The PSA-PCL-HA micelles possessed a modestly increased size (~150 nm) and comparable polydispersity relative to PSA-PCL micelles. A small size, with limited variability, is critical to the development of an effective drug delivery system with reproducible pharmacokinetic behavior.

Lovastatin and simvastatin were successfully entrapped within the PSA-PCL-HA micelles. High performance liquid chromatography (HPLC) was used to quantify the amount of micelle encapsulated statin. Both statins were incorporated into the micelles with high loading capacities of ~0.1 mg/mg, defined by the mass of statin per mass of PSA-PCL-HA, and high loading efficiencies of ~60%, defined as the percentage of statin encapsulated in the micelles relative to the total amount of statin available for encapsulation. Of note, the loading capacity of the statin-loaded PSA-PCL-HA micelles was equal to or greater than those found with other hydrophobic drug-micelle systems. This observation is expected to translate to a low requisite dose in the treatment of PAD.

To verify that modification with HA enhances uptake by VSMCs, PSA-PCL and PSA-PCL-HA were fluorescently tagged with Alexa Fluor 610. VSMCs were seeded into collagen-coated plates and stimulated with IL-1β (10 ng/ml) to induce CD44 expression (24 h, 37° C.). Then, fluorescently labeled micelles were added. Rinsing and imaging 60 minutes post-administration revealed that cells exposed to PSA-PCL-HA displayed a greater amount of red fluorescence than those treated with PSA-PCL, as seen in FIG. 11. The latter result suggests that HA does enhance cellular uptake, as expected, and that the PSA-PCL-HA micelle system is suitable to enhance the retention of statins upon intraluminal administration.

To demonstrate that the statins retained bioactivity when encapsulated within PSA-PCL-HA micelles, simvastatin (SV) and simvastatin-loaded micelles (SV+micelles) over a range of concentrations were administered to IL-1β (10 ng/ml) stimulated VSMCs. After 24 hours, changes in the proliferation of cells exposed to statins and statin-loaded micelles were assessed relative to untreated control cells using a WST-8 assay (Cayman). As seen in FIG. 12, the $IC_{50}$ value obtained for micelle encapsulated simvastatin was nearly identical to that of free simvastatin.

Example 3

A number of conventional, disease modifying anti-rheumatic drugs (DMARDs) are associated with severe side effects due to non-specific targeting and/or impaired immune function. To improve therapeutic efficacy and reduce negative consequences, PSA-PCL micelles may be used for site-specific delivery to the synovial tissue.

PSA-based micelles were prepared via self-assembly of hydrophilic polysialic acid with hydrophobic polycaprolactone (PSA-PCL), as previously described. Dynamic light scattering and transmission electron microscopy validated formation of stable micelles with a size of 100 nm and low polydispersity. To facilitate active targeting of the CD44 HA receptor that is upregulated on RASFs within the inflamed joint tissue, HA oligomers were attached to a small percentage (<1%) of the PSA monomers of PSA-PCL through an adipic dihydrazide (ADH) tether, as seen in FIG. 14. The PSA-PCL-HA micelles possessed a modestly increased size (~150 nm) and comparable polydispersity relative to PSA-PCL micelles. A small size, with limited variability, is critical to the application of an effective drug delivery system with reproducible pharmacokinetic behavior. Dexamethasone, a conventional disease modifying anti-rheumatic drug (DMARD), was successfully entrapped within the PSA-PCL-HA micelles at a loading capacity of 0.1 mg DM/mg PSA-PCL-HA.

The DM-loaded, PSA-based micelles were administered intravenously to mice with collagen-induced arthritis (CIA) every 3 days following disease onset. Twenty-four male, DBA/1J mice were divided into four treatment groups: non-diseased, diseased (with no drug therapy), free DM (3.0 mg DM/kg), and DM-loaded micelle (3.0 mg PSA-PCL-HA/kg~0.3 mg DM/kg). At day 28 following induction of collagen-induced arthritis (CIA) in 18 of the 24 mice, each mouse was scored for arthritis index (AI). The AI of mice that received the DM-loaded micelles was comparable to the AI obtained from mice that received free DM at a ten times higher relative dose, as seen in FIG. 14. The AI, also denoted as the clinical score, is calculated as the sum of scores assigned to describe the severity of inflammation on each paw of a given mouse, as described in Table 2. The results establish that the targeted, PSA-based micelles can increase the therapeutic index of associated bioactive molecules. More particularly, DM loaded into the PSA-PCL-HA micelles was as effective as free DM when administered at ¹⁄₁₀th the dose to mice with CIA.

What is claimed is:

1. A delivery system for a therapeutic compound, comprising a micelle having a backbone of polymerized sialic acid monomers and amine terminated polycaprolactone grafted to a portion of the sialic acid monomers, wherein the sialic acid monomers and polycaprolactone are present in a weight ratio of 4 to 1.

2. The system of claim 1, wherein the portion of sialic acid monomers that are grafted with the amine terminated polycaprolactone is about one percent.

3. The system of claim 2, wherein the micelles have a diameter of 73.8+/−14.2 nanometers at a concentration of 1 milligram per milliliter and a temperature of 25° C.

4. The system of claim 1, further comprising a therapeutic compound loaded into the micelles.

5. The system of claim 1, wherein the therapeutic compound is loaded to a capacity of 0.1 milligrams per milligram of micelle.

6. The system of claim 1, further comprising a receptor agonist tethered to a portion of the sialic acid monomers.

7. The system of claim 6, wherein the receptor agonist comprises a hyaluronic acid oligomer tethered to a plurality of the sialic acid monomers.

8. The system of claim 7, wherein the hyaluronic acid oligomer is tethered to less than one percent of the sialic acid monomers.

9. The system of claim 8, wherein the hyaluronic acid oligomer is tethered to the plurality of the sialic acid monomers by an adipic dihydrazide.

10. The system of claim 9, further comprising an anti-rheumatic drug loaded into the micelles.

11. The system of claim 10, wherein the anti-rheumatic drug comprises dexamethasone.

12. The system of claim 11, wherein the drug is loaded to a capacity of 0.1 milligrams per milligram of micelle.

13. The system of claim 11, wherein the micelles loaded with dexamethasone have a diameter of about 150 nanometers.

14. A method of delivering a therapeutic compound comprising the steps of loading the therapeutic compound into the system of claim 1 and administering the loaded micelles to a patient.

* * * * *